United States Patent [19]
Antonucci et al.

[11] Patent Number: 6,046,222
[45] Date of Patent: *Apr. 4, 2000

[54] USE OF THIAZOLIDINEDIONE DERIVATIVES IN THE TREATMENT OF POLYCYSTIC OVARY SYNDROME, GESTATIONAL DIABETES AND DISEASE STATES AT RISK FOR PROGRESSING TO NONINSULIN-DEPENDENT DIABETES MELLITUS

[75] Inventors: Tammy Antonucci, Thousand Oaks, Calif.; Dean Lockwood, Ann Arbor; Rebecca Norris, Kewadin, both of Mich.

[73] Assignee: Warner-Lambert Company, Morris Plains, N.J.

[*] Notice: This patent is subject to a terminal disclaimer.

[21] Appl. No.: 08/868,608

[22] Filed: Jun. 4, 1997

Related U.S. Application Data

[63] Continuation-in-part of application No. 08/856,987, May 15, 1997, which is a continuation-in-part of application No. 08/763,286, Dec. 10, 1996, which is a division of application No. 08/469,398, Jun. 6, 1995, Pat. No. 5,602,133, which is a division of application No. 08/292,585, Aug. 23, 1994, Pat. No. 5,457,109, which is a continuation-in-part of application No. 08/122,251, Sep. 15, 1993.

[51] Int. Cl.[7] .................................................. A61K 31/425
[52] U.S. Cl. ............................................................ 514/369
[58] Field of Search ............................................. 514/369

[56] References Cited

U.S. PATENT DOCUMENTS

| | | | |
|---|---|---|---|
| 4,287,200 | 9/1981 | Kawamatsu et al. | 424/270 |
| 4,572,912 | 2/1986 | Yoshioka et al. | 514/369 |
| 4,687,777 | 8/1987 | Meguro et al. | 514/342 |
| 4,873,255 | 10/1989 | Yoshioka et al. | 514/369 |
| 4,897,405 | 1/1990 | Alessi et al. | 514/360 |
| 5,061,717 | 10/1991 | Clark et al. | 514/342 |
| 5,120,754 | 6/1992 | Clark et al. | 514/369 |
| 5,132,317 | 7/1992 | Cantello et al. | 514/369 |
| 5,223,522 | 6/1993 | Clark et al. | 514/369 |
| 5,457,109 | 10/1995 | Antonucci et al. | . |
| 5,602,133 | 2/1997 | Antonucci et al. | . |

FOREIGN PATENT DOCUMENTS

| | | |
|---|---|---|
| 0 306 228 A1 | 3/1989 | European Pat. Off. . |
| 0332332 | 9/1989 | European Pat. Off. . |
| 0415605 | 3/1991 | European Pat. Off. . |
| 0419035 | 3/1991 | European Pat. Off. . |
| 9112003 | 8/1991 | WIPO . |
| 9207838 | 5/1992 | WIPO . |
| 9207839 | 5/1992 | WIPO . |
| 9300343 | 1/1993 | WIPO . |
| 95/07694 | 3/1995 | WIPO . |
| 95/07697 | 3/1995 | WIPO . |

OTHER PUBLICATIONS

PCT International Search Report, PCT/US98/10472, Mailed Sep. 25, 1998.
Leroith, D., et al.: "Diabetes Mellitus" 1996, Lippincott–Raven, Philadelphia, XP002077274, p. 661–668, and Whitcomb, R.W., et al., "New Therapies for Non–insulin–Dependent Diabetes Mellitus: Thiazolidinediones" Chapter 74, 1996.
Ooshima, Y. and Ihara, T., "Embryopathy in Genetically Diabetic Mice, Yellow KK, and its Prevention by Maternal Therapy" Cong. Anom., 1986, vol. 26, No. 3, pp. 169–177.
Bloomgarden, Z.T., "American Diabetes Association Annual Meeting 1996: The Etiology of Type II Diabetes, Obesity, and the Treatment of Type II Diabetes" Diabetes Care, Nov. 1996, vol. 19, No. 11, pp. 1311–1315.
*The New England Journal of Medicine*, vol. 319, No. 23, 1988, pp. 1500–1506, Saad et al.
*Diabetes Care*, vol. 15, No. 8, 1992, pp 1075–1078, Hofmann et al.
*J. Med. Chem.*, vol. 35, No. 14, 1992, pp 2617–2626, Sohda et al.
*Chemical Abstracts*, vol. 119, No. 1, 1993, abstract No. 97.
*Annals of the New York Academy of Sciences*, vol. 687, 1993, pp 60–64, Dunaif.
*Annales d'Endocrinologie (Paris)*, vol. 53, No. 1, 1992, pp 1–7, Dewailly et al.
*Diabetologia*, vol. 34, 1991, p. A198, Robinson et al.
PCT International Search Report, PCT/US 94/10187.
*Drugs*, 44 (Suppl. 3):29–38, 1992, Lefebvre et al.
*The Lancet*, 1:870–872, 1988, Polson et al.
*Obstetrics & Gynecology*, 66:545–552, 1985, Dunaif et al.
*Metabolism*, 38:1089–1093, 1989, Kraegen et al.
*Diabetes*, 37:1549–1558, 1988, Fujiwara et al.
*Diabetes Res. and Clin. Practice*, 11:147–153, 1991, Kuzaza et al.
*Diabetes Care*, 15:193–203, 1992, Suter et al.
*Diabetes Care*, 14:1083–1086, 1991, Iwamoto et al.

*Primary Examiner*—James H. Reamer
*Attorney, Agent, or Firm*—Charles W. Ashbrook

[57] ABSTRACT

Novel methods of using thiazolidinone derivatives and related antihyperglycemic agents to treat populations at risk for developing noninsulin-dependent diabetes mellitus (NIDDM) and complications arising therefrom are disclosed. In one embodiment, the compounds of the invention are used to treat polycystic ovary syndrome in order to prevent or delay the onset of noninsulin-dependent diabetes mellitus. In another embodiment, the compounds of the invention are used to treat gestational diabetes in order to prevent or delay the onset of noninsulin-dependent diabetes mellitus.

3 Claims, No Drawings

USE OF THIAZOLIDINEDIONE DERIVATIVES IN THE TREATMENT OF POLYCYSTIC OVARY SYNDROME, GESTATIONAL DIABETES AND DISEASE STATES AT RISK FOR PROGRESSING TO NONINSULIN-DEPENDENT DIABETES MELLITUS

This application is a continuation-in-part of U.S. patent application Ser. No. 08/856,987, filed May 15, 1997, which is a continuation-in-part of U.S. patent application Ser. No. 08/763,286, filed Dec. 10, 1996; which is a divisional application of U.S. Ser. No. 08/469,398, filed Jun. 6, 1995, now U.S. Pat. No. 5,602,133, issued Feb. 11, 1997; which is a divisional application of U.S. Ser. No. 08/292,585, filed Aug. 23, 1994, now U.S. Pat. No. 5,457,109, issued Oct. 10, 1995; which is a continuation-in-part of U.S. Ser. No. 08/122,251, filed Sep. 15, 1993.

FIELD OF THE INVENTION

The present invention pertains to a number of compounds which can be used to treat certain disease states in order to prevent or delay the onset of noninsulin-dependent diabetes mellitus (NIDDM). More specifically, the present invention involves in one embodiment administering to a patient certain known thiazolidinedione derivatives and related antihyperglycemic agents which treat disease states such as polycystic ovary and gestational diabetes syndrome which are at increased risk in the development of NIDDM, thus preventing or delaying the onset of NIDDM or complications resulting therefrom.

BACKGROUND OF THE INVENTION

Diabetes is one of the most prevalent chronic disorders worldwide with significant personal and financial costs for patients and their families, as well as for society. Different types of diabetes exist with distinct etiologies and pathogeneses. For example, diabetes mellitus is a disorder of carbohydrate metabolism, characterized by hyperglycemia and glycosuria and resulting from inadequate production or utilization of insulin.

NIDDM, or otherwise referred to as Type II diabetes, is the form of diabetes mellitus which occurs predominantly in adults in whom adequate production of insulin is available for use, yet a defect exists in insulin-mediated utilization and metabolism of glucose in peripheral tissues. Overt NIDDM is characterized by three major metabolic abnormalities: resistance to insulin-mediated glucose disposal, impairment of nutrient-stimulated insulin secretion, and overproduction of glucose by the liver. It has been shown that for some people with diabetes a genetic predisposition results in a mutation in the gene(s) coding for insulin and/or the insulin receptor and/or insulin-mediated signal transduction factor(s), thereby resulting in ineffective insulin and/or insulin-mediated effects thus impairing the utilization or metabolism of glucose.

Reports indicate that insulin secretion is often enhanced early-on, presumably as compensation for the insulin resistance. People who actually develop NIDDM appear to do so because their B-cells eventually fail to maintain sufficient insulin secretion to compensate for the insulin resistance. Mechanisms responsible for the B-cell failure have not been identified, but may be related to the chronic demands placed on the B-cells by peripheral insulin resistance and/or to the effects of hyperglycemia to impair B-cell function. The B-cell failure could also occur as an independent, inherent defect in "pre-diabetic" individuals.

NIDDM often develops from certain at risk populations, one such population is individuals with polycystic ovary syndrome (PCOS). PCOS is the most common endocrine disorder in women of reproductive age. This syndrome is characterized by hyperandrogenism and disordered gonadotropin secretion producing oligo- or anovulation. Recent prevalence estimates suggest that 5–10% of women between 18–44 years of age (about 5 million women, according to the 1990 census) have the full-blown syndrome of hyperandrogenism, chronic anovulation, and polycystic ovaries. Despite more than 50 years since its original description, the etiology of the syndrome remains unclear. The biochemical profile, ovarian morphology, and clinical features are non-specific; hence, the diagnosis remains one of exclusion of disorders, such as androgen-secreting tumors, Cushing's Syndrome, and late-onset congenital adrenal hyperplasia.

PCOS is associated with profound insulin resistance resulting in substantial hyperinsulinemia. As a result of their insulin resistance, PCOS women are at increased risk to develop NIDDM. Hirsutism, acne, and alopecia, which are commonly found in PCOS women, are clinical manifestations of hyperandrogenism. Menstrual disturbances and infertility are the result of ovulatory dysfunction related to the disordered gonadotropin secretion. Androgen excess, probably by eventual conversion of androgens to estrogen, also plays an important role in disrupting gonadotropin release in PCOS.

There are two leading hypotheses for the association between PCOS and insulin resistance: 1) androgens produce insulin resistance or 2) hyperinsulinemia produces hyperandrogenism. In support of the first hypothesis, synthetic androgen administration can increase insulin levels in women. However, in PCOS women with acanthosis nigricans (which is a marker for insulin resistance), oophorectomy lowers testosterone levels but does not alter insulin resistance. Further, long-acting GnRH agonist treatment in PCOS women decreases plasma testosterone and androstenedione levels into the normal female range, but does not alter glucose tolerance, insulin levels, or insulin action. Thus, although certain synthetic androgens may have a modest effect on insulin sensitivity, natural androgens do not produce insulin resistance of the magnitude found in PCOS.

In contrast, there are several lines of evidence that support the alternative hypothesis that hyperinsulinemia produces hyperandrogenism. First, extreme insulin resistance of a variety of etiologies, ranging from insulin receptor mutations to autoimmune insulin resistance, is associated with ovarian hyperandrogenism. Second, insulin can directly stimulate ovarian androgen secretion in vitro and in vivo in PCOS women. Finally, decreasing insulin levels for 10 days with diazoxide results in a significant decrease in testosterone levels in PCOS women. Insulin does not alter gonadotropin release but rather appears to act directly on the ovary. However, these actions of insulin are not observed in normal ovulatory women, suggesting that polycystic ovarian changes are necessary for such insulin effects to be manifested.

Insulin resistance in PCOS is secondary to a marked decrease in insulin receptor-mediated signal transduction and a modest, but significant, decrease in adipocyte GLUT4 content. In many PCOS women, the decrease in insulin receptor signaling is the result of intrinsic abnormalities in insulin receptor phosphorylation. The magnitude of insulin resistance in PCOS is similar to that in NIDDM and in obesity. However, the cellular mechanisms of insulin resistance appear to differ in PCOS compared to these other common insulin-resistant states. The shift to the right in the insulin dose-response curve for adipocyte glucose uptake is much more striking in PCOS than in obesity. Further, decreases in adipocyte insulin sensitivity and responsiveness are significantly correlated with hyperinsulinemia, glycemia, and/or obesity in individuals with NIDDM or obesity, whereas insulin resistance is independent of these parameters in PCOS. Finally, no persistent abnormalities in insulin receptor autophosphorylation have been identified in NIDDM or obesity.

NIDDM also develops from the at risk population of individuals with gestational diabetes mellitus (GDM). Pregnancy normally is associated with progressive resistance to insulin-mediated glucose disposal. In fact, insulin sensitivity is lower during late pregnancy than in nearly all other physiological conditions. The insulin resistance is thought to be mediated in large part by the effects of circulating hormones such as placental lactogen, progesterone, and cortisol, all of which are elevated during pregnancy. In the face of the insulin resistance, pancreatic B-cell responsiveness to glucose normally increases nearly 3-fold by late pregnancy, a response that serves to minimize the effect of insulin resistance on circulating glucose levels. Thus, pregnancy provides a major "stress-test" of the capacity for B-cells to compensate for insulin resistance.

Studies of insulin action and B-cell function during pregnancy indicate that, during the third trimester, women with mild-moderate GDM have the same degree of insulin resistance as do non-diabetic pregnant women. However, studies during the second trimester and after pregnancy indicate that women with GDM are somewhat insulin resistant compared to women who maintain normal glucose tolerance during pregnancy. Taken together, the available data indicate that pancreatic B-cells of women who develop GDM may encounter two types of insulin resistance: 1) mild-moderate, underlying, and perhaps genetic insulin resistance that is present even when the women are not pregnant; and 2) the marked, physiological (probably hormonally-mediated) insulin resistance that occurs during pregnancy in all women. Data indicate that the main feature which distinguishes women with GDM from normal pregnant women during the third trimester, when all women are insulin resistant, is pancreatic B-cell function. Most women develop GDM because their pancreatic B-cells are unable to maintain enhanced insulin secretion in the face of insulin resistance. That inability is very similar to the B-cell defect which has been observed in longitudinal studies of patients who develop NIDDM, a fact which may explain why women with GDM are at such high risk for NIDDM: GDM identifies women whose B-cells will decompensate when faced with severe or chronic insulin resistance.

Other populations thought to be at risk for developing NIDDM are persons with Syndrome X; persons with concomitant hyperinsulinemia; persons with insulin resistance characterized by hyperinsulinemia and by failure to respond to exogenous insulin; and persons with abnormal insulin and/or evidence of glucose disorders associated with excess circulating glucocorticoids, growth hormone, catecholamines, glucagon, parathyroid hormone, and other insulin-resistant conditions.

Failure to treat NIDDM can result in mortality due to cardiovascular disease and in other diabetic complications including retinopathy, nephropathy, and peripheral neuropathy. For many years treatment of NIDDM has involved a program aimed at lowering blood sugar with a combination of diet and exercise. Alternatively, treatment of NIDDM involved oral hypoglycemic agents, such as sulfonylureas alone or in combination with insulin injections. Recently, alpha-glucosidase inhibitors, such as a carboys, have been shown to be effective in reducing the postprandial rise in blood glucose (Lefevre, et al., *Drugs* 1992;44:29–38). In Europe and Canada another treatment used primarily in obese diabetics is metformin, a biguanide.

In any event, what is required is a method of treating at risk populations such as those with PCOS and GDM in order to prevent or delay the onset of NIDDM thereby bringing relief of symptoms, improving the quality of life, preventing acute and long-term complications, reducing mortality and treating accompanying disorders of the populations at risk for NIDDM. The methods of using the disclosed compounds for treating at risk populations with conditions such as PCOS and GDM to prevent or delay the onset of NIDDM as taught herein meet these objectives.

The compounds of the present invention, and methods of making the compounds, are known and some of these are disclosed in U.S. Pat. Nos. 5,223,522 issued Jun. 29, 1993; 5,132,317 issued Jul. 12, 1992; 5,120,754 issued Jun. 9, 1992; 5,061,717 issued Oct. 29, 1991; 4,897,405 issued Jan. 30, 1990; 4,873,255 issued Oct. 10, 1989; 4,687,777 issued Aug. 18, 1987; 4,572,912 issued Feb. 25, 1986; 4,287,200 issued Sep. 1, 1981; 5,002,953, issued Mar. 26, 1991; U.S. Pat. Nos. 4,340,605; 4,438,141; 4,444,779; 4,461,902; 4,703,052; 4,725,610; 4,897,393; 4,918,091; 4,948,900; 5,194,443; 5,232,925; and 5,260,445; WO 91/07107; WO 92/02520; WO 94/01433; WO 89/08651; and JP Kokai 69383/92. The compounds disclosed in these issued patents and applications are useful as therapeutic agents for the treatment of diabetes, hyperglycemia, hypercholesterolemia, and hyperlipidemia. The teachings of these issued patents and applications are incorporated herein by reference.

Regarding prevention of NIDDM, there has been one disclosure of this concept using a sulfonylurea as a treatment, but this concept is not highly regarded in the scientific community because prolonged treatment with sulfonylureas can reduce insulin secretion by destroying the pancreatic beta cells. Moreover, sulfonylureas can cause clinically severe hypoglycemia. The concept of using a biguanide, such as metformin, has also been disclosed.

There is no disclosure in the above-identified references to suggest the use of the compounds identified in this present application in the treatment of at risk populations such as those with PCOS or GDM in order to prevent or delay the onset of NIDDM and complications resulting therefrom.

SUMMARY OF THE INVENTION

In one embodiment of this invention, a method is disclosed for the treatment of PCOS in order to prevent or delay the onset of NIDDM. Improvement in insulin sensitivity by treatment with the compounds of the following formulas will reduce fasting insulin levels, thereby resulting in decreased androgen production and biologic availability in PCOS women. Decreasing androgen levels will improve the clinical symptoms of androgen excess and the anovulation commonly found in PCOS women.

In another embodiment of this invention, a method is disclosed for the treatment of GDM. Improvement in whole-body insulin sensitivity by treatment with the compounds of the following formulas will reduce the rate of B-cell decomposition and delay or prevent the development of NIDDM in women with GDM. The compounds can also be applied to former gestational diabetic women to delay or prevent NIDDM and its long-term complications. As agents having the aforementioned effects, the compounds of the following formulas are useful in treating individuals to prevent or delay the onset of NIDDM.

In another embodiment of the present invention is a method for treating population states, other than those with PCOS or GDM, who are at risk for developing NIDDM. Other populations thought to be at risk for developing NIDDM are persons with Syndrome X; persons with concomitant hyperinsulinemia; persons with insulin resistance characterized by hyperinsulinemia and by failure to respond to exogenous insulin; and persons with abnormal insulin and/or evidence of glucose disorders associated with excess circulating glucocorticoids, growth hormone, catecholamines, glucagon, parathyroid hormone, and other insulin-resistant conditions. Treatment of the above populations with the compounds of the following formulas will prevent or delay the onset of NIDDM.

Accordingly, the present invention is the use of compounds of Formula I

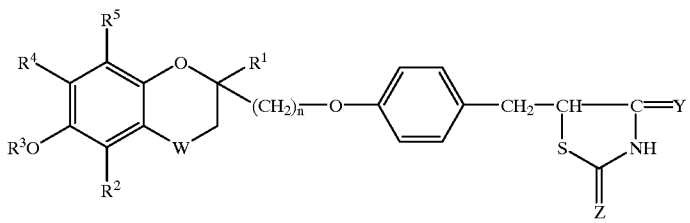

I herein $R^1$ and $R^2$ are the same or different and each represents a hydrogen atom or a $C_1$–$C_5$ alkyl group;

$R^3$ represents a hydrogen atom, a $C_1$–$C_6$ aliphatic acyl group, an alicyclic acyl group, an aromatic acyl group, a heterocyclic acyl group, anaraliphatic acyl group, a ($C_1$–$C_6$ alkoxy)carbonyl group, or an aralkyloxycarbonyl group;

$R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group;

n is 1, 2, or 3;

W represents the —$CH_2$—, >CO, or CH—$OR^6$ group (in which $R^6$ represents any one of the atoms or groups defined for $R^3$ and may be the same as or different from $R^3$); and Y and Z are the same or different and each represents an oxygen atom or an imino (ÍNH) group;

and pharmaceutically acceptable salts thereof.

The present invention is also the use of compounds of the Formula II

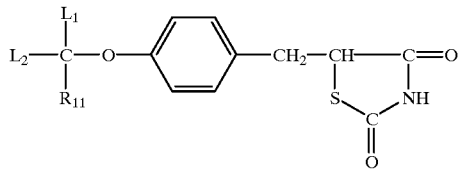

II wherein $R_{11}$ is substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula

wherein $R_{13}$ and $R_{14}$ are the same or different and each is lower alkyl or $R_{13}$ and $R_{14}$ are combined to each other either directly or as interrupted by a heteroatom selected from the group consisting of nitrogen, oxygen, and sulfur to form a 5- or 6-membered ring;

wherein $R_{12}$ means a bond or a lower alkylene group; and wherein $L_1$ and $L_2$ are the same or different and each is hydrogen or lower alkyl or $L_1$ and $L_2$ are combined to form an alkylene group; or a pharmaceutically acceptable salt thereof.

The present invention is also the use of compounds of the Formula III

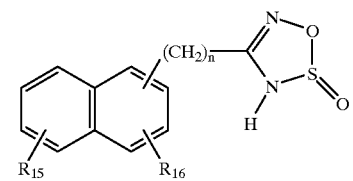

III wherein $R_{15}$ and $R_{16}$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4 and the pharmaceutically acceptable salts thereof.

The present invention is also directed to the use of compounds of the Formula IV

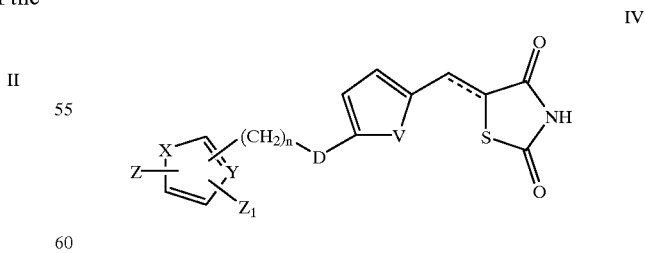

IV wherein the dotted line represents a bond or no bond;
V is —CH=CH—, —N=CH—, —CH=N— or S;
D is $CH_2$, CHOH, CO, C=$NOR_{17}$ or CR=CH;
X is S, O, $NR_{18}$, —CH=N or —N=CH;
Y is CH or N;
Z is hydrogen, ($C_1$–$C_7$) alkyl, ($C_3$–$C_7$)cycloalkyl, phenyl, naphthyl, pyridyl,furyl, thienyl, or phenyl mono- or disubstituted with the same or different groups which are $(C_1-C_3)$ alkyl, trifluoromethyl, $(C_1-C_3)$alkoxy, fluoro, chloro, or bromo;

$Z_1$ is hydrogen or $(C_1-C_3)$alkyl;

$R_{17}$ and $R_{18}$ are each independently hydrogen or methyl; and n is 1, 2, or 3; the pharmaceutically acceptable cationic salts thereof; and the pharmaceutically acceptable acid addition salts thereof when the compound contains a basic nitrogen.

The present invention is also directed to the use of compounds of the Formula V

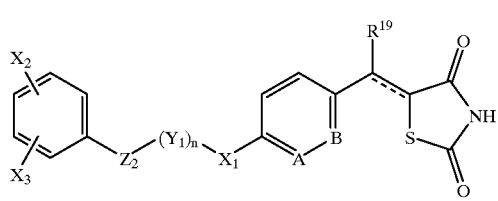
V wherein the dotted line represents a bond or no bond;

A and B are each independently CH or N, with the proviso that when A or B is N, the other is CH;

$X_1$ is S, SO, $SO_2$, $CH_2$, CHOH, or CO;

n is 0 or 1;

$Y_1$ is $CHR_{20}$ or $R_{21}$, with the proviso that when n is 1 and $Y_1$ is $NR_{21}$, $X_1$ is $SO_2$ or CO;

$Z_2$ is

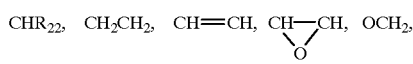

$OCH_2$, $SCH_2$, $SOCH_2$ or $SO_2CH_2$;

$R_{19}$, $R_{20}$, $R_{21}$, and $R_{22}$ are each independently hydrogen or methyl; and $X_2$ and $X_3$ are each independently hydrogen, methyl, trifluoromethyl, phenyl, benzyl, hydroxy, methoxy, phenoxy, benzyloxy, bromo, chloro, or fluoro; a pharmaceutically acceptable cationic salt thereof; or a pharmaceutically acceptable acid addition salt thereof when A or B is N.

The present invention also relates to the use of compounds of the Formula VI

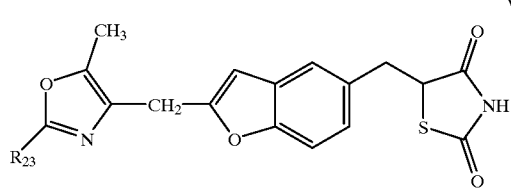
VI or a pharmaceutically acceptable salt thereof wherein $R_{23}$ is alkyl of 1 to 6 carbon atoms, cycloalkyl of 3 to 7 carbon atoms, phenyl or mono- or di-substituted phenyl wherein said substituents are independently alkyl of 1 to 6 carbon atoms, alkoxy of 1 to 3 carbon atoms, halogen, or trifluoromethyl.

The present invention also provides the use of a compound of Formula VII

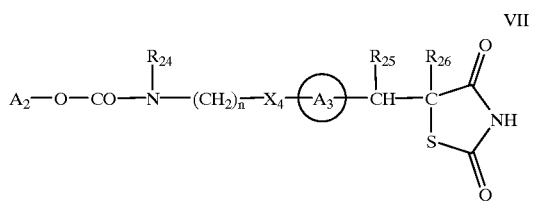
VII or a tautomeric form thereof and/or a pharmaceutically acceptable salt thereof, and/or a pharmaceutically acceptable solvate thereof, wherein:

$A_2$ represents an alkyl group, a substituted or unsubstituted aryl group, or an aralkyl group wherein the alkylene or the aryl moiety maybe substituted or unsubstituted;

$A_3$ represents a benzene ring having in total up to 3 optional substituents;

$R_{24}$ represents a hydrogen atom, an alkyl group, an acyl group, an aralkyl group wherein the alkyl or the aryl moiety maybe substituted or unsubstituted, or a substituted or unsubstituted aryl group; or $A_2$ together with $R_{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group;

$R_{25}$ and $R_{26}$ each represent hydrogen, or $R_{25}$ and $R_{26}$ together represent a bond;

$X_4$ represents O or S; and n represents an integer in the range of from 2 to 6.

The present invention also provides the use of a compound of Formula VIII

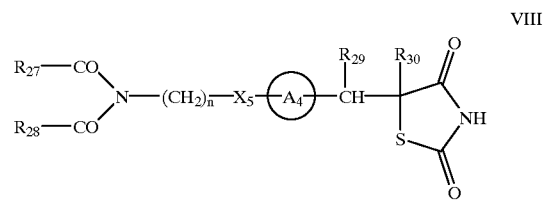
VIII or a tautomeric form thereof and/or a pharmaceutically acceptable salt thereof, and/or a pharmaceutically acceptable solvate therefor, wherein:

$R_{27}$ and $R_{28}$ each independently represent an alkyl group, a substituted or unsubstituted aryl group, or an aralkyl group being substituted or unsubstituted in the aryl or alkyl moiety; or $R_{27}$ together with $R_{28}$ represents a linking group, the linking group consisting of an optionally substituted methylene group and either a further optionally substituted methylene group or an O or S atom, optional substituents for the said methylene groups being selected from alkyl, aryl, or aralkyl, or substituents of adjacent methylene groups together with the carbon atoms to which they are attached form a substituted or unsubstituted phenylene group;

$R_{29}$ and $R_{30}$ each represent hydrogen, or $R_{29}$ and $R_{30}$ together represent a bond;

$A_4$ represents a benzene ring having in total up to 3 optional substituents;

$X_5$ represents O or S; and n represents an integer in the range of from 2 to 6.

The present invention also provides the use of a compound of Formula IX

IX

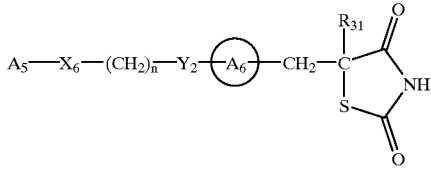

or a tautomeric form thereof and/or a pharmaceutically acceptable salt thereof, and/or a pharmaceutically acceptable solvate thereof, wherein:

$A_5$ represents a substituted or unsubstituted aromatic heterocyclyl group;

$A_6$ represents a benzene ring having in total up to 5 substituents;

$X_6$ represents O, S, or $NR_{32}$ wherein $R_{32}$ represents a hydrogen atom, an alkyl group, an acyl group, an aralkyl group, wherein the aryl moiety maybe substituted or unsubstituted, or a substituted or unsubstituted aryl group;

$Y_2$ represents O or S;

$R_{31}$ represents an alkyl, aralkyl, or aryl group; and n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur, or nitrogen.

Favored aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2, or 3 heteroatoms, especially 1 or 2, selected from oxygen, sulphur, or nitrogen.

Suitable values for $A_5$ when it represents a 5-membered aromatic heterocyclyl group include thiazolyl and oxazoyl, especially oxazoyl.

Suitable values for $A_5$ when it represents a 6-membered aromatic heterocyclyl group include pyridyl or pyrimidinyl.

Suitable $R_{31}$ represents an alkyl group, in particular a $C_{1-6}$ alkyl group, for example a methyl group. Preferably, $A_5$ represents a moiety of formula (a), (b), or (c):

(a)

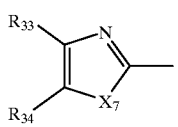

(b)

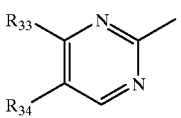

(c)

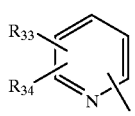

wherein:

$R_{33}$ and $R_{34}$ each independently represents a hydrogen atom, an alkyl group, or a substituted or unsubstituted aryl group or when $R_{33}$ and $R_{34}$ are each attached to adjacent carbon atoms, then $R_{33}$ and $R_{34}$ together with the carbon atoms to which they are attached form a benzene ring wherein each carbon atom represented by $R_{33}$ and $R_{34}$ together may be substituted or unsubstituted; and in the moiety of Formula (a), $X_7$ represents oxygen or sulphur.

In one favored aspect $R_{33}$ and $R_{34}$ together represent a moiety of Formula (d):

(d)

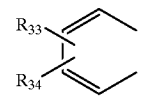

wherein $R_{35}$ and $R_{36}$ each independently represent hydrogen, halogen, substituted or unsubstituted alkyl, or alkoxy.

The present invention also provides for the use of compounds for Formula X

X

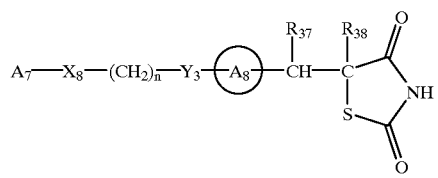

or a tautomeric form thereof and/or a pharmaceutically acceptable salt thereof, and/or a pharmaceutically acceptable solvate thereof, wherein:

$A_7$ represents a substituted or unsubstituted aryl group;

$A_8$ represents a benzene ring having in total up to 5 substituents;

$X_8$ represents O, S, or $NR_{39}$ wherein $R_{39}$ represents a hydrogen atom, an alkyl group, an acyl group, an aralkyl group, wherein the aryl moiety maybe substituted or unsubstituted, or a substituted or unsubstituted aryl group;

$Y_3$ represents O or S;

$R_{37}$ represents hydrogen;

$R_{38}$ represents hydrogen or an alkyl, aralkyl, or aryl group or $R_{37}$ together with $R_{38}$ represents a bond; and n represents an integer in the range of from 2 to 6.

A still further embodiment of the present invention is the use of a pharmaceutical composition for administering an effective amount of a compound of the preceding Formulas I through X along with a pharmaceutically acceptable carrier in unit dosage form in the treatment methods mentioned above.

DETAILED DESCRIPTION OF THE PREFERRED EMBODIMENTS

The compounds used in the treatment methods of the invention, which are 5-[4-(chromoanalkoxy)benzyl] thiazolidene derivatives, may be represented by the Formulas (Ia), (Ib), and (Ic)

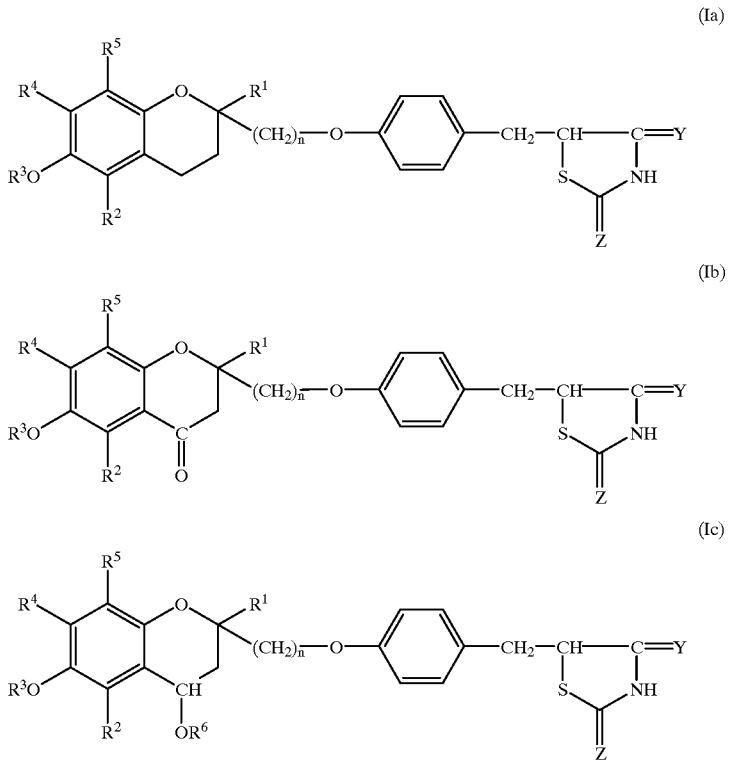

(in which $R^1$, $R^2$, $R^3$, $R^4$, $R^5$, $R^6$, n, Y, and Z are as defined above) and include pharmaceutically acceptable salts thereof.

In the compounds of the invention, where $R^1$ or $R^2$ represents an alkyl group, this may be a straight or branched chain alkyl group having from 1 to 5 carbon atoms and is preferably a primary or secondary alkyl group, for example the methyl, ethyl, propyl, isopropyl, butyl, isobutyl, pentyl, or isopentyl group.

Where $R^3$, $R^6$, or $R^{6'}$ represents an aliphatic acyl group, this preferably has from 1 to 6 carbon atoms and may include one or more carbon—carbon double or triple bonds. Examples of such groups include the formyl, acetyl, propionyl, butyryl, isobutyryl, pivaloyl, hexanoyl, acryloyl, methacryloyl, and crotonyl groups.

Where $R^3$, $R^6$, or $R^{6'}$ represents an alicyclic acyl group, it is preferably a cyclopentanecarbonyl, cyclohexanecarbonyl, or cycloheptanecarbonyl group.

Where $R^3$, $R^6$, or $R^{6'}$ represents an aromatic acyl group, the aromatic moiety thereof may optionally have one or more substituents (for example, nitro, amino, alkylamino, dialkylamino, alkoxy, halo, alkyl, or hydroxy substituents); examples of such aromatic acyl groups included the benzoyl, p-nitrobenzoyl, m-fluorobenzoyl, o-chlorobenzoyl, p-aminobenzoyl, m-(dimethylamino)benzoyl, o-methoxybenzoyl, 3,4-dichlorobenzoyl, 3,5-di-t-butyl-4-hydroxybenzoyl, and 1-naphthoyl groups.

Where $R^3$, $R^6$, or $R^{6'}$ represents a heterocyclic acyl group, the heterocyclic moiety thereof preferably has one or more, preferably one, oxygen, sulfur, or nitrogen hetero atoms and has from 4 to 7 ring atoms; examples of such heterocyclic acyl groups include the 2-furoyl, 3-thenoyl, 3-pyridinecarbonyl (nicotinoyl), and 4-pyridinecarbonyl groups.

Where $R^3$, $R^6$, or $R^{6'}$ represents an araliphatic acyl group, the aliphatic moiety thereof may optionally have one or more carbon-carbon double or triple bonds and the aryl moiety thereof may optionally have one or more substituents (for example, nitro, amino, alkylamino, dialkylamino, alkoxy, halo, alkyl, or hydroxy substituents); examples of such araliphatic acyl groups include the phenylacetyl, p-chlorophenylacetyl, phenylpropionyl, and cinnamoyl groups.

Where $R^3$, $R^6$, or $R^{6'}$ represents a ($C_1$–$C_6$ alkoxy)carbonyl group, the alkyl moiety thereof may be any one of those alkyl groups as defined for $R^1$ and $R^2$, but is preferably a methyl or ethyl group, and the alkoxycarbonyl group represented by $R^3$, $R^6$, or $R^{6'}$ is therefore preferably a methoxycarbonyl or ethoxycarbonyl group.

Where $R^3$, $R^6$, or $R^{6'}$ represents an aralkyloxycarbonyl group, the aralkyl moiety thereof may be any one of those included within the araliphatic acyl group represented by $R^3$, $R^6$, or $R^{6'}$, but is preferably a benzyloxycarbonyl group.

Where $R^4$ and $R^5$ represent alkyl groups, they may be the same or different and may be straight or branched chain alkyl groups. They preferably have from 1 to 5 carbon atoms and examples include the methyl, ethyl, propyl, isopropyl, butyl, isobutyl, t-butyl, pentyl, and isopentyl groups.

Where $R^4$ and $R^5$ represent alkoxy groups, these may be the same or different and may be straight or branched chain groups, preferably having from 1 to 4 carbon atoms. Examples include the methoxy, ethoxy, propoxy, isopropoxy, and butoxy groups. Alternatively, $R^4$ and $R^5$ may together represent a $C_1$–$C_4$ alkylenedioxy group, more preferably a methylenedioxy or ethylenedioxy group.

Preferred classes of compounds of Formula I are as follows:

(1) Compounds in which $R^3$ represents a hydrogen atom, a $C_1$–$C_6$ aliphatic acyl group, an aromatic acyl group, or a heterocyclic acyl group.

(2) Compounds in which Y represents an oxygen atom; $R^1$ and $R^2$ are the same or different and each represents a hydrogen atom or a $C_1$–$C_5$ alkyl group; $R^3$ represents a hydrogen atom, a $C_1$–$C_6$ aliphatic acyl group, an aromatic acyl group, or a pyridinecarbonyl group; and $R^4$ and $R^5$ are the same or different and each represents a hydrogen atom, a $C_1$–$C_5$ alkyl group, or a $C_1$ or $C_2$ alkoxy group.

(3) Compounds as defined in (2) above, in which: $R^1$, $R^2$, $R^4$, and $R^5$ are the same or different and each represents a hydrogen atom or a $C_1$–$C_5$ alkyl group; n is 1 or 2; and W represents the —$CH_2$— or >CO group.

(4) Compounds as defined in (3) above, in which $R^3$ represents a hydrogen atom, a $C_1$–$C_5$ aliphatic acyl group, a benzoyl group, or a nicotinyl group.

(5) Compounds as defined in (4) above, in which: $R^1$ and $R^4$ are the same or different and each represents a $C_1$ $C_5$ alkyl group; $R^2$ and $R^5$ are the same or different and each represents the hydrogen atom or the methyl group; and $R^3$ represents a hydrogen atom or a $C_1$ $C_4$ aliphatic acyl group.

(6) Compounds in which: W represents the —$CH_2$— or >CO group; Y and Z both represent oxygen atoms; n is 1 or 2; $R^1$ and $R^4$ are the same or different and each represents a $C_1$–$C_4$ alkyl group; $R^2$ and $R^5$ are the same or different and each represents the hydrogen atom or the methyl group; and $R^3$ represents a hydrogen atom or a $C_1$–$C_4$ aliphatic acyl group.

(7) Compounds as defined in (6) above, in which n is 1.

(8) Compounds as defined in (6) or (7) above, in which W represents the —$CH_2$_group.

Preferred compounds among the compounds of Formula I are those wherein:

$R^1$ is a $C_1$–$C_4$ alkyl group, more preferably a methyl or isobutyl group, most preferably a methyl group;

$R^2$ is a hydrogen atom or a $C_1$–$C_4$ alkyl group, preferably a hydrogen atom, or a methyl or isopropyl group, more preferably a hydrogen atom or a methyl group, most preferably a methyl group;

$R^3$ is a hydrogen atom, a $C_1$–$C_4$ aliphatic acyl group, an aromatic acyl group or a pyridinecarbonyl group, preferably a hydrogen atom, or an acetyl, butyryl, benzoyl, or nicotinyl group, more preferably a hydrogen atom or an acetyl, butyryl or benzoyl group, most preferably a hydrogen atom or an acetyl group;

$R^4$ is a hydrogen atom, a $C_1$–$C_4$ alkyl group or a $C_1$ or $C_2$ alkoxy group, preferably a methyl, isopropyl, t-butyl, or methoxy group, more preferably a methyl or t-butyl group, most preferably a methyl group;

$R^5$ is a hydrogen atom, a $C_1$–$C_4$ alkyl group or a $C_1$ or $C_2$ alkoxy group, preferably a hydrogen atom, or a methyl or methoxy group, more preferably a hydrogen atom or a methyl group, and most preferably a methyl group;

n is 1 or 2, preferably 1;

Y is an oxygen atom;

Z is an oxygen atom or an imino group, most preferably an oxygen atom; and

W is a —$CH_2$_ or >CÍO group, preferably a —$CH_2$ group.

Referring to the general Formula II, the substituents may be any from 1 to 3 selected from nitro, amino, alkylamino, dialkylamino, alkoxy, halo, alkyl, or hydroxy, the aromatic acyl group maybe benzoyl and naphthoyl. The alkyl group $R_{11}$ may be a straight chain or branched alkyl of 1 to 10 carbon atoms, such as methyl, ethyl, n-propyl, i-propyl, n-butyl, i-butyl, t-butyl, n-pentyl, i-pentyl, n-hexyl, n-heptyl, n-octyl, n-nonyl, and n-decyl; the cycloalkyl group $R_{11}$ may be a cycloalkyl group of 3 to 7 carbon atoms, such as cyclopropyl, cyclopentyl, cyclohexyl, and cycloheptyl; and the phenylalkyl group $R_{11}$ may be a phenylalkyl group of 7 to 11 carbon atoms such as benzyl and phenethyl. As examples of the heterocyclic group $R_1$ 1 may be mentioned 5- or 6-membered groups each including 1 or 2 hetero-atoms selected from among nitrogen, oxygen, and sulfur, such as pyridyl, thienyl, furyl, thiazolyl, etc. When $R_{11}$ is

the lower alkyls $R_{13}$ and $R_{14}$ may each be a lower alkyl of 1 to 4 carbon atoms, such as methyl, ethyl, n-propyl, i-propyl, and n-butyl. When $R_{13}$ and $R_{14}$ are combined to each other to form a 5- or 6-membered heterocyclic group as taken together with the adjacent N atom, ie, in the form of

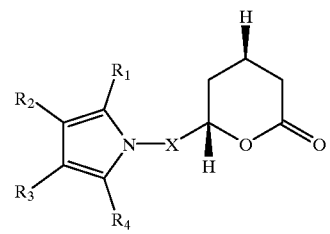

this heterocyclic group may further include a heteroatom selected from among nitrogen, oxygen, and sulfur as exemplified by piperidino, morpholino, pyrrolidino, and piperazino. The lower alkylene group $R_{12}$ may contain 1 to 3 carbon atoms and thus may be, for example, methylene, ethylene, or trimethylene. The bond $R_{12}$ is equivalent to the symbol "-", ".", or the like which is used in chemical structural formulas, and when $R_{12}$ represents such a bond, the compound of general Formula II is represented by the following general Formula II(a)

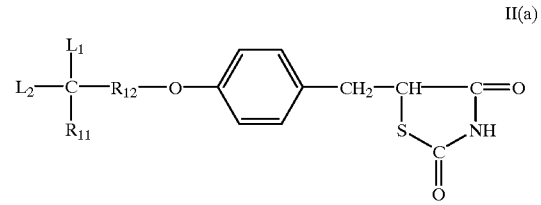

Thus, when $R_{12}$ is a bond, the atoms adjacent thereto on both sides are directly combined together. As examples of the lower alkyls $L_1$ and $L_2$, there may be mentioned lower alkyl groups of 1 to 3 carbon atoms, such as methyl and ethyl. The alkylene group formed as $L_1$ and $L_2$ are joined together is a group of the formula —$(CH_2)_n$- [where n is an integer of 2 to 6]. The cycloalkyl, phenylalkyl, phenyl, and heterocyclic groups mentioned above, as well as said heterocyclic group may have 1 to 3 substituents in optional positions on the respective rings. As examples of such substituents may be mentioned lower alkyls (eg, methyl, ethyl, etc.), lower alkoxy groups (eg, methoxy, ethoxy, etc.), halogens (eg, chlorine, bromine, etc.), and hydroxyl. The case also falls within the scope of the general Formula II that an alkylenedioxy group of the formula —O—$(CH_2)_m$-O— [is an integer of 1 to 3], such as methylenedioxy, is attached to the two adjacent carbon atoms on the ring to form an additional ring.

The preferred compounds of Formula III are those wherein $R_{15}$ and $R_{16}$ are independently hydrogen, lower alkyl containing 1 to 6 carbon atoms, alkoxy containing 1 to 6 carbon atoms, halogen, ethynyl, nitrile, trifluoromethyl, vinyl, or nitro; n is 1 or 2 and the pharmaceutically acceptable salts thereof.

Preferred in Formula IV are compounds wherein the dotted line represents no bond, particularly wherein D is CO or CHOH. More preferred are compounds wherein V is —CH=CH—, —CH=N— or S and n is 2, particularly those compounds wherein X is O and Y is N, X is S and Y is N, X is S and Y is CH or X is —CH=N— and Y is CH. In the most preferred compounds X is O or S and Y is N forming an oxazol-4-yl, oxazol-5-yl, thiazol-4-yl, or thiazol-5-yl group; most particularly a 2-[(2-thienyl), (2-furyl), phenyl, or substituted phenyl]-5-methyl-4-oxazolyl group.

The preferred compounds in Formula V are:

a) those wherein the dotted line represents no bond, A and B are each CH, $X_1$ is CO, n is 0, $R_{19}$ is hydrogen, $Z_2$ is $CH_2CH_2$ or CHCH and $X_3$ is hydrogen, particularly when $X_2$ is hydrogen, 2-methoxy, 4-benzyloxy, or 4-phenyl;

b) those wherein A and B are each CH, $X_1$ is S or $SO_2$, n is 0, $R_{19}$ is hydrogen, $Z_2$ is $CH_2CH_2$ and $X_3$ is hydrogen, particularly when $X_2$ is hydrogen or 4-chloro.

A preferred group of compounds is that of Formula VI wherein $R_{23}$ is $(C_1-C_6)$alkyl, $(C_3-C_7)$cycloalkyl, phenyl, halophenyl, or $(C_1-C_6)$alkylphenyl. Especially preferred within this group are the compounds where $R_{23}$ is phenyl, methylphenyl, fluorophenyl, chlorophenyl, or cyclohexyl.

When used herein with regard to Formulas VII through X, the term "aryl" includes phenyl and naphthyl, suitably phenyl, optionally substituted with up to 5, preferably up to 3, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

The term "halogen"refers to fluorine, chlorine, bromine, and iodine; preferably chlorine.

The terms "alkyl" and "alkoxy" relate to groups having straight or branched carbon chains, containing up to 12 carbon atoms.

Suitable alkyl groups are $C_{1-12}$ alkyl groups, especially $C_{1-6}$ alkyl groups, eg, methyl, ethyl, n-propyl, iso-propyl, n-butyl, isobutyl, or tert-butyl groups.

Suitable substituents for any alkyl group include those indicated above in relation to the term "aryl".

Suitable substituents for any heterocyclyl group include up to 4 substituents selected from the group consisting of alkyl, alkoxy, aryl, and halogen or any 2 substituents on adjacent carbon atoms, together with the carbon atoms to which they are attached, may form an aryl group, preferably a benzene ring, and wherein the carbon atoms of the aryl group represented by the said 2 substituents may themselves be substituted or unsubstituted.

Specific examples of compounds of the present invention are given in the following list:

(+)-5-[[4-[(3,4-dihydro-6-hydroxy-2,5,7,8-tetramethyl-2H-1-benzopyran-2-yl)methoxy]phenyl]methyl]-2,4-thiazolidinedione;

4-(2-naphthylmethyl)- 1,2,3,5-oxathiadiazole-2-oxide;

5-[4-[2-[N-(benzoxazol-2-yl)-N-methylamino]ethoxy] benzyl]-5-methyl-thiazolidine-2,4-dione;

5-[4-[2-[2,4-dioxo-5-phenylthiazolidin-3-yl)ethoxy] benzyl]thiazolidine-2,4-dione;

5-[4-[2-[N-methyl-N-(phenoxycarbonyl)amino]ethoxy] benzyl]-thiazolidine-2,4-dione;

5- [4-(2-phenoxyethoxy)benzyl]thiazolidine-2,4-dione;

5-[4-[3-(5-methyl-2-phenyloxazol-4-yl)propionyl]benzyl ]thiazolidine-2,4-dione;

5-[4-[2-(4-chlorophenyl)ethylsulfonyl]benzyl] thiazolidine-2,4-dione;

5-[4- [3 -(5-methyl-2-phenyloxazol-4-yl)propionyl] benzyl]thiazolidine-2,4-dione; and 5-(4-[2-(N-methyl-N-(2-pyridyl)amino)-ethoxy]benzyl) 2,4-thiazolidinedione.

As defined herein, "complications of NIDDM" is referred to as cardiovascular complications or several of the metabolic and circulatory disturbances that are associated with hyperglycemia, eg, insulin resistance, hyperinsulinemia and/or hyperproinsulinemia, delayed insulin release, dyslipidemia, retinopathy, peripheral neuropathy, nephropathy, and hypertension.

The compounds of Formulas I through X are capable of further forming pharmaceutically acceptable base salts.

The compounds of Formulas I through X are capable of further forming both pharmaceutically acceptable acid addition and/or base salts. All of these forms are within the scope of the present invention.

Pharmaceutically acceptable acid addition salts of the compounds of Formulas I through X include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge S. M., et al., "Pharmaceutical Salts," *Journal of Pharmaceutical Science* 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *Journal of Pharmaceutical Science* 1977;66:1–19).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in different configurations. The compounds can, therefore, form stereoisomers. Although these are all represented herein by a limited number of molecular formulas, the present invention includes the use of both the individual, isolated isomers and mixtures, including racemates, thereof. Where stereospecific synthesis techniques are employed or optically active compounds are employed as starting materials in the preparation of the compounds, individual isomers may be prepared directly; on the other hand, if a mixture of isomers is prepared, the individual isomers may be obtained by conventional resolution techniques, or the mixture may be used as it is, without resolution.

Furthermore, the thiazolidene part of the compound of Formulas I through X can exist in the form of tautomeric isomers. All of the tautomers are represented by Formulas I through X, and are intended to be a part of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use in the treatment of at risk populations such as those with impaired glucose tolerance, to prevent or delay the onset of NIDDM and complications arising therefrom, the compounds utilized in the pharmaceutical methods of this invention are administered along with a pharmaceutically acceptable carrier at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage maybe divided and administered in portions during the day, if desired.

The following nonlimiting examples illustrate the inventors' preferred methods for preparing the compounds of the invention.

The compounds of Formulas I through X are valuable agents in returning an individual to a state of glucose tolerance and therefore preventing or delaying the onset of NIDDM. Tests were conducted which showed that compounds of Formulas I through X possess the disclosed activity. The tests employed on the compounds of Formulas I through X were performed by the following study.

EXAMPLE 1

A study will be performed to determine the effect of troglitazone ((+)-5-[[4-[(3,4-dihydro-6-hydroxy-2,5,7,8- tetramethyl-2H-1-benzopyran-2-yl)-methoxy]phenyl]methyl]-2,4-thiazolidinedione) on insulin resistance and androgen levels in PCOS women. Since hyperandrogenism results in chronic anovulation and hirsutism, decreasing androgen levels may improve hirsutism and even restore normal ovulatory menstrual function in PCOS women. The specific aim of the study will be to determine the effects of improved insulin sensitivity and decreased insulin levels secondary to troglitazone treatment on circulating androgen and gonadotropin levels in PCOS women.

I. SUBJECTS

A. General Selection Criteria. A total of 30 women will be studied. All subjects will be in excellent health, between the ages of 18–45 years, and euthyroid. There will be no history of cardiorespiratory, hepatic, or renal dysfunction. No subject will be taking any medications known to affect reproductive hormone levels or carbohydrate metabolism for at least 1 month prior to study, with the exception of oral contraceptives, which will be discontinued 3 months prior to study. Obesity will be defined as body mass index (BMI: wt (kg)/hr$^2$(m) of $\geq$27 kg/m$^2$, non-obese patients will have a BMI of $\leq$25 kg/m$^2$.

B. Selection criteria for PCOS. The diagnosis of PCOS will require biochemically documented hyperandrogenism (serum levels of testosterone, biologically available testosterone, and/or androstenedione two standard deviations or more above the control mean), chronic anovulation (<6 menses/year or dysfunctional uterine bleeding), and polycystic ovaries present on vaginal ovarian ultrasound. These are the least controversial criteria for diagnosis for PCOS. The LH:FSH ratio and hirsutism will not be used as selection criteria. Androgen secreting tumors, Cushing's Syndrome, and late-onset congenital adrenal hyperplasia will be excluded by appropriate tests in all women. Women with hyperprolactinemia will be excluded because of the possible effect of hyperprolacticemia on insulin sensitivity.

C. Disqualification Criteria
1. Pregnancy
2. Intercurrent medical illness
3. Hepatic or renal dysfunction
4. Hemoglobin <11 gm/dL
5. Weight <50 kg.

II. STUDY PROTOCOL

A. Subject Preparation for All Studies. All testing will be performed during a period of documented anovulation by plasma progesterone levels in PCOS women. Subjects will consume a 55% carbohydrate, 30% fat, 15% protein weight maintaining diet for 3 days prior to testing and all testing will be done in the post-absorptive state after 10–12 hours fast.

B. Protocol
1. Visit 1—Day 1. A complete history and physical examination will be performed and blood for a complete blood count, electrolytes, thyroid function (thyroid profile with TSH level), renal chemistries and liver function will be obtained. Blood for testosterone (T), biologically available T (uT), LH, FSH, dehydroepiandrosterone sulfate (DHEAS), androstenedione (A), sex hormone binding globulin (SHBG), estrone (E$_1$), estradiol (E$_2$), insulin, and C-peptide levels will be obtained. A 75 g glucose load will be ingested in the morning after a 10–12 hr fast, and glucose and insulin levels will be obtained every 30 minutes for 2 hours.

All PCOS women will have fasting insulin levels $\geq$15 $\mu$U/mL and may have impaired glucose tolerance by WHO criteria. No subject, however, will have diabetes mellitus.

| | WHO Diagnostic Criteria | | |
|---|---|---|---|
| Serum Glucose mg/dL (mmol/L) | Normal | IGT | Diabetes |
| Fasting | <140 (<7.8) | <140 (<7.8) | $\geq$140 ($\geq$7.8) |
| 2 hour | <140 (<7.8) | 140–199 (7.8–11.1) | $\geq$200 ($\geq$11.1) |

2. Visit 1—Day 2. A frequently sampled intravenous glucose tolerance test (FSIGT) will be performed. Basal blood samples will be collected at −15, −10, −5, and −1 minute. Glucose (300 mg/kg) will be injected as an IV bolus at time 0 minute and tolbutamide (500 mg) will be injected at 20 minutes. Blood samples will be taken at 2, 3, 4, 5, 8, 10, 12, 14, 16, 19, 22, 23, 24, 25, 27, 30, 40, 50, 60, 70, 90, 100 minutes, and every 20 minutes thereafter until 240 minutes for glucose and insulin levels.

3. Troglitazone therapy. Troglitazone will be started after Visit 1, Day 2, when a urine pregnancy test will be documented to be negative. Troglitazone will be administered in a double-blind randomized trial of two dose levels: 200 mg/day and 400 mg/day. Subjects will be randomly assigned to one of the two daily doses of troglitazone. All women will take two pills: either two 200 mg pills or a 200 mg pill and a placebo pill. There will be 15 subjects in each of the two treatment groups. Troglitazone will be administered as a single daily dose with breakfast.

4. Visits 2 and 3. Subjects will return monthly. Blood will be obtained every 10 minutes×3 and the plasma pooled for assay of T, $\mu$T, A, DHEAS, SHBG, E$_2$, E$_1$, LH, and FSH levels. Insulin and glucose levels basally and 2hours after 75 g glucose will be determined.

5. Visit 4. The studies performed at Visit 1 will be repeated. Subjects will be instructed to return all unused supplies or empty bottles at the time of each visit to ensure compliance. Details related to patient dosage and compliance will be recorded on the case report form.

III. STATISTICAL ANALYSIS

Each subject will serve as her own control, and the data will be analyzed by paired t-test. Differences in treatment vs baseline hormone levels and parameters of insulin action will be compared between the two dose groups by unpaired t-tests. Repeated measures of analysis of variance will be performed to determine changes over time. Log transformation of the data will be performed when necessary to achieve homogeneity of variance. This is a pilot study and 15 PCOS women each will be examined at two dose levels of troglitazone.

IV. HUMAN SUBJECTS

A. Risks
1. Blood Withdrawal. All subjects will have normal a complete blood count and hemoglobin levels >11 mg/dL. No subject will have >500 mL blood drawn in 24-hour period and >1000 mL blood drawn over 12-week period.

2. FSIGT. There is a small risk of hypoglycemia during FSIGT, and the test will be terminated immediately by administration of 50% dextrose if signs or symptoms of severe hypoglycemia develop. There is a small risk of allergy to tolbutamide; the drug will not be given to any subject with a history of allergy to sulfa drugs or sulfonylureas.

3. Troglitazone. The major side effects of troglitazone are nausea, peripheral edema, and abnormal liver function. Other reported adverse events include dyspnea, headache, thirst, gastrointestinal distress, insomnia, dizziness, incoordination, confusion, fatigue, pruritus, rash, alterations in blood cell counts, changes in serum lipids, acute renal insufficiency, and dryness of the mouth. Additional symptoms that have been reported, for which the relationship to troglitazone is unknown, include palpitations, sensations of hot and cold, swelling of body parts, skin eruption, stroke, and hyperglycemia.

4. Disqualification Criteria. Subjects will be disqualified if they will develop one or more of the following: HB <11 gm/dL, wt <50 kg, abnormal hepatic or renal chemistries, hypertension, pregnancy, significant illnesses, or excessive bleeding.

The demonstration that treatment with troglitazone will reduce the rate of NIDDM in patients with GDM will have important clinical and biological significance. The clinical significance is the obvious potential for treatment of GDM patients to prevent or delay overt diabetes and its long-term complications. The choice of an agent that improves insulin action may not only reduce the risk of diabetic complications that clearly are related to chronic metabolic decompensation (ie, retinopathy, hephropathy, and neuropathy), but also may reduce the risk of cardiovascular complications such as hypertension and atherosclerosis, that have been associated with insulin resistance and hyperinsulinemia. The biological significance of a reduced rate of diabetes during treatment with troglitazone will depend to some extent on the effects of the drug on insulin action.

To test the hypothesis that interventions to improve whole-body insulin sensitivity will reduce the rate of B-cell decompensation and delay or prevent the development of NIDDM, a randomized, double-blind, placebo-controlled trial of troglitazone will be performed. The trial will be performed among individuals at high risk for NIDDM such as women with a history of GDM. In particular, because the age-adjusted prevalence rates of NIDDM among Hispanic women aged 24–64 years have been reported to be 8–11%, rates which are 2–3 times those of non-Hispanic whites in the U.S., the test will be performed among Hispanic women.

|  | History Physical | EKG | Pregnancy Test | Chemistry[a] | Hormones[b] | OGTT | FSIGT | Timing |
|---|---|---|---|---|---|---|---|---|
| Visit 1 - Day 1 | X | X |  | X | X | X |  | Baseline |
| Visit 1 - Day 2 |  |  | X |  |  |  | X | Baseline |
| Visit 2 | X |  | X |  | X | X |  | 1 month |
| Visit 3 | X |  | X |  | X | X |  | 2 months |
| Visit 4 - Day 1 | X | X |  | X | X | X |  | 3 months |
| Visit 4 - Day 2 |  |  | X |  |  |  | X | 3 months |

[a]Chemistry - Complete blood count with differential, electrolytes, liver function, renal function, thyroid profile with TSH level
[b]Hormones - T, $\mu$T, LH, FSH, DHEAS, SHBG, P, A, $E_2$, $E_1$, insulin, C-peptide levels

EXAMPLE 2

Thiazolidinediones have been shown to increase insulin sensitivity in insulin-resistant, non-diabetic and diabetic animals and in humans with NIDDM. Several thiazolidinediones are undergoing testing in the US, including studies of proglitizone in fructose-fed rats and obese rhesus monkeys. The drugs appear to improve insulin sensitivity in skeletal muscle and liver, major sites of insulin resistance in NIDDM. In response to the increased insulin sensitivity, which has been in the range of 40–100% above pretreatment levels, pancreatic B-cells appear to down-regulate insulin secretion, so that hyperinsulinemia is reduced and hypoglycemia is not a risk. Of the possible pharmacological interventions, thiazolidinediones appear well-suited for testing in the prevention of NIDDM in patients whose underling insulin resistance is thought to lead to B-cell decompensation and diabetes. Therefore, it is proposed to test the effects of a thiazolidinedione that has been shown to increase insulin sensitivity in people with NIDDM, on insulin sensitivity and NIDDM rates in our very high-risk patients with recent GDM.

In particular, it is proposed to test the effects of the agent, troglitazone, that has been shown to enhance insulin-mediated glucose disposal in humans. While not wishing to be bound by theory, if the hypothesis is correct, troglitazone will maintain insulin action at a level which is commensurate with B-cell reserve in some, and perhaps many subjects, thereby preventing or delaying the development of NIDDM.

I. OVERVIEW OF STUDY DESIGN

Hypothesis: Troglitazone will improve insulin sensitivity and delay or prevent NIDDM in Latino women with a history of GDM who are at very high risk for NIDDM.

Patients: ~230 Hispanic women with recent GDM and a glucose tolerance test at 6-12 weeks postpartum indicating a very high risk of developing NIDDM within 3-5 years (ie, total glucose area >16.3 gm.min/dL).

Procedures:

1. Measure whole-body insulin sensitivity (minimal model $S_1$) at baseline.
2. Randomize to drug or placebo (double-blind design).
3. Measure insulin sensitivity after 4 and 24 months on treatment.
4. Follow for development of NIDDM:
   a. Fasting glucose at 4-month intervals
   b. Oral glucose tolerance test annually
   c. Mean follow-up of 36 months.

Analysis:

1. Between group (drug and placebo) comparison of cumulative NIDDM rates using life table methods:
   a) by intent-to-treat
   b) by response-to-therapy.
2. Between group comparison of 4-month changes in $S_1$ using 2-group t-test; between group changes in $S_1$ over time using repeated measures ANOVA.

3. Within and between group analysis of factors associated with any reduction in NIDDM rate using Cox proportional hazards regression analysis.

II. INTERVENTION TRIAL: SUBJECT SELECTION AND ENROLLMENT

A. Inclusion and Exclusion Criteria

INCLUSION: Age 18–45 years, recent GDM by the National Diabetes Data Group criteria, *Diabetes*, 29:1039–1057 (1979), singleton pregnancy, Mexican-American or Central-American (self-declared ethnicity); both parents and ¾ grandparents of Mexican or Central American heritage, residence within 60 minutes of LAC Medical Center, 6–12 week postpartum OGTT glucose area >16.3 gm.min/dL.

EXCLUSION: Plans for pregnancy within 4 years, medical illness requiring chronic medications that alter glucose tolerance or that will preclude 3–4 years of follow-up (eg, malignancy, HIV infection), illicit drug abuse, inability to give informed consent.

III. SPECIFIC PROCEDURES

A. OGTT

1. Procedure: Sitting subjects will have an indwelling antecubital venous catheter placed in the morning after a 10–12 hour fast. At least 30 minutes later, dextrose (75 g) will be given orally over 5 minutes. Blood will be drawn at −10, 30, 60, 90, and 120 minutes from the start of the dextrose ingestion.
2. Interpretation: OGTTs plasma glucose concentrations will be interpreted according to National Diabetes Data Group criteria.
3. Risks: Limited to those of an intravenous line (pain, infection, bruising/bleeding at site), nausea at the time of dextrose ingestion, and phlebotomy (15 mL blood).

B. IVGTT

1. Procedure: After an overnight fast, subjects will be placed at bedrest and will have bilateral antecubital venous catheters placed. At least 30 minutes later, a basal blood sample will be drawn and dextrose (300 mg/kg body weight) will be given intravenously over 1 minute. An intravenous injection of tolbutamide (3 mg/kg) will be given 20 minutes after the dextrose injection. Plasma samples will be obtained at 2, 4, 8, 14, 19, 22, 30, 40, 50, 70, 100, and 180 minutes after the glucose injection and assayed for glucose and insulin.
2. Analysis: Insulin sensitivity will be calculated by computer analysis of the glucose and insulin patterns during the IVGTT.
3. Risks: Hypoglycemia is a potential complication following tolbutamide injection. However, tolbutamide is injected when the plasma glucose is high, so that hypoglycemia is unusual. It has never been observed in over 50 IVGTTs in Hispanic women using the 3 mg/kg tolbutamide dose. Nonetheless, patients will be observed for symptoms of hypoglycemia and stop the test if symptomatic hypoglycemia (<60 mg/dL) occurs. Risks of intravenous lines and phlebotomy (total =39 mL) are minimal. Persons with a hematocrit <33% will not be studied with the IVGTT.

C. Body Morphometry

1. Procedures: Body weight will be measured on a standard beam balance (subjects lightly clothed, without shoes). Height will be measured with a statometer. Waist circumference will be measured at the minimum circumference between the thorax and the iliac crest. Hip circumference will be measured at the level of the maximum posterior protrusion of the buttocks.
2. Interpretation: Body mass index will be calculated as: [weight in kg]/[height in meters] and used as a surrogate for measures of adiposity. The ratio of the waist circumference to the hip circumference will be calculated as a measure of fat distribution. Each measure will be tested as a predictive feature for NIDDM and for any effects of therapy on NIDDM risk.
3. Risks: None.

D. Blood Pressure

Blood pressure will be measured in triplicate in sitting (×5 minutes) patients with an aeriod sphygmomanometer. First and fourth Korotkoff sounds will be used to determine systolic and diastolic BP. There are no risks associated with the procedure.

E. Assays

1. Insulin: Insulin is measured in plasma with a charcoal precipitation radioimmunoassay using human insulin standard, guinea pig anti-porcine insulin antibodies, and tyrosine A-19 iodoinsulin purchased from Novo-Nordisk. Quality control will be maintained. RIA has a mean interassay coefficient of variation of 12% at 7±3 $\mu$U/mL and 7% at 32±6 $\mu$U/mL, based on pooled plasma samples stored at −70° C. over a period of 12 months.
2. Glucose: Glucose will be measured in duplicate by glucose oxidase (Beckman Glucose Analyzer II).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of preventing or delaying the onset of noninsulin dependent diabetes mellitus comprising administering to a host suffering from polycystic ovary syndrome or having suffered from gestational diabetes a therapeutically effective amount of the compound 5-[p-[2-(5-ethyl-2-pyridyl)ethoxy]benzyl]-2,4-thiazolidinedione (Pioglitazone).

2. A method of treating polycystic ovary syndrome, the method comprising administering to a host suffering from polycystic ovary syndrome a therapeutically effective amount of the compound 5-[p-[2-(5-ethyl-2-pyridyl)ethoxy] benzyl]-2,4-thiazolidinedione (Pioglitazone).

3. A method of treating gestational diabetes, the method comprising administering to a host suffering from gestational diabetes a therapeutically effective amount of the compound 5-[p-[2-(5-ethyl-2-pyridyl)ethoxy]benzyl]-2,4-thiazolidinedione (Pioglitazone).

* * * * *